US 6,590,092 B1

(12) United States Patent
Ngo

(10) Patent No.: US 6,590,092 B1
(45) Date of Patent: Jul. 8, 2003

(54) PROCESS FOR PREPARING A "UNIVERSAL SUPPORT" AND THE REAGENTS USED FOR GENERATING SUCH SUPPORT

(76) Inventor: Nam Q. Ngo, 4191 Rineon Ave., Campbell, CA (US) 95008

( * ) Notice: Subject to any disclaimer, the term of this patent is extended or adjusted under 35 U.S.C. 154(b) by 0 days.

(21) Appl. No.: 09/314,603

(22) Filed: May 19, 1999

Related U.S. Application Data

(60) Provisional application No. 60/088,507, filed on Jun. 8, 1998, and provisional application No. 60/086,041, filed on May 19, 1998.

(51) Int. Cl.[7] .............................................. C07H 21/02
(52) U.S. Cl. ........................ 536/25.3; 536/89; 530/322; 530/333; 530/334; 530/335; 525/54.2
(58) Field of Search .................. 536/25.3, 89; 530/322, 530/333, 334, 335; 535/54.2

(56) References Cited

U.S. PATENT DOCUMENTS 4,659,774 A    4/1987  Webb et al.

FOREIGN PATENT DOCUMENTS

WO         WO 95/01987        1/1995

*Primary Examiner*—Bennett Celsa

(57) ABSTRACT

Universal solid supports suitable for use synthesizing of oligonucleotides. The solid supports may be used irrespective of the first RNA or DNA nucleotide to be synthesized, and irrespective of the type of monomer reagent used during the synthesis, that is, irrespective of the type of substitution of the phosphate group in the 3' position or in the 5' position depending on whether the synthesis is carried out in the 5' to 3' or 3' to 5' direction. Following synthesis of the oligonucleotide, deprotection of protecting groups and cleavage of the oligonucleotide from the solid support is accomplished with treatment with standard basic media such as $NH_4OH$, NaOH, methylamine.

17 Claims, No Drawings

US 6,590,092 B1

PROCESS FOR PREPARING A "UNIVERSAL SUPPORT" AND THE REAGENTS USED FOR GENERATING SUCH SUPPORT

This application claims the benefit of provisional application Ser. No. 60/088,507 filed on Jun. 8, 1998 and application Ser. No. 60/086,041 filed on May 19, 1998.

FIELD OF THE INVENTION

The present invention relates generally to the synthesis of nucleic acids and more particularly relates to solid supports that are useful in automated synthesis of DNA or RNA oligonucleotides.

BACKGROUND OF THE INVENTION

Universal Solid supports used in automated oligonucleotide synthesis possess pre-attached nucleosides to provide a chain initiation site for oligonucleotide construction. Chain elongation occurs by sequential addition of monomeric phosphoramidite unites on the 5' hydroxyl. During the deprotection process of the oligodeoxyribonucleotide, the pre-attached nucleoside is cleaved from the solid support and retained on the oligodeoxyribonucleotide as the 3'-terminated base. Solid supports suitable for automated synthesis of oligonucleotides must satisfy the following characteristics:

1) the solid support must react selectively with the functionalized 3' end of the nucleotide in particular of the phosphoramidite, H-phosphonate, phosphotiester, phosphodiester, phosphite type or with any other monomer reagent according to the synthetics method used;
2) the support-oligonucleotide bond must be stable under the conditions of the synthesis;
3) the support oligonucleotide bond must be able to be hydrolyzed at the end of the synthesis under the conditions for the step of deprotection of the oligonucleotide; and
4) the covalent bond between the support and oligonucleotide must be such that, during the detachment, the released oligonucleotide must be such that, during the detachment, the release oligonucleotide is of native type, that is to say that the 3' terminal hydroxyl function is free or does not bear any residue derived from the synthesis.

Many supports have already been described in the literature for the solid phase synthesis of oligonucleotides. These supports may consist of organic polymers such as polystyrene (Nucleic A. Res. 1980, Vol. 8), polyacrylamide acryloylmorpholide, polydimethyl acrylamide polymerized on kieselfuhr (Nucleic Acid Res. 9(7) 1691 (1980)). Other supports described are of inorganic nature, in particular based on silica functionalized with a hydrocarbon radical bearing an $NH_2$ and/or COOH group (JACS, 105, 661 (1983), or the support based on silica functionalized with a 3-aminopropyltriethoxysilane group whose use in phosphite and phosphoramidite synthesis for the preparation of oligonucleotides described for the first time in European patent No. 0,035,719.

Typically, when employing prior art solid supports, the first step in synthesizing nucleic acids consists of attaching the first nucleoside of the desired sequence to the solid support, traditionally consisting of glass beads of controlled porosity (CPG) or, more generally, of a functionalized organic or inorganic polymer bound to an A, T, C, G or U nucleoside, depending on whether the sequence to be prepared contains A, T, C, G, or U as the first deoxyribo-or ribonucleoside. Thus, commercially available automated reactors are equipped so that one of these nucleosides has already been attached to the support. The appropriate reactor is thus selected depending on whether the sequence begins with A, T, C, G, or U. Elongation of this first nucleoside then takes place in the 3' to 5' or 5' to 3' direction, by means of coupling reagents. One synthetic cycle, that is to say the coupling between two nucleotides, includes at least three steps: (1) deprotection of the 5' or 3' OH function of a first nucleotide, e.g., detritylation, (2) activation of the said 5' or 3' OH function of this nucleotide and condensation with the 3' or 5' end respectively of a second nucleotide, and, finally, (3) oxidation of the phosphite group of the internucleotide bond obtained to phosphate.

The oligonucleotide is preferable synthesized in the 3' to 5' direction. In this case, the staring material is a 5' OH-protected nucleoside that is attached to the support via the 3' end of the deoxyribose or ribose ring. The nucleotides which are subsequently added are in the form of a 5'-protected derivative whose 3' hydroxyl possesses a substituted phosphite or phosphate group.

Various synthetic methods are currently employed and the are distinguished by the type of substitution on the phosphate. The phosphoramidite method, described, for example, in EP 0,061,746 and U.S. Pat. No. 4,458,066, is the preferred technique because of the high coupling yields achieved. In this method, a phosphoramidite group is attached to the 3' hydroxyl. Besides the importance of these groups for the solubility of the nucleosides in the organic solvent, the phosphoramidite group renders the phosphorus atom more susceptible to attack by a primary hydroxyl function, such as that in the 5' position of the detritylated growing nucleosides or chains. The deprotected 5' hydroxyl function becomes sufficiently nucleophilic to react with the phosphoramidite group of the second nucleotide.

The oligonucleotides obtained at the end of the synthetic cycles must be detached from the support and the protective functions must be removed. Cleavage of the support, deprotection of the bases and removal of the group bonded to the phosphorus are carried out simultaneously in aqueous ammonia solution. In the case of RNA, ethanol makes it possible to solubilize the 2'-O-silyl-oligoribonucleotides, and to minimize the desilylation as native RNA is not stable in basic conditions. The aqueous ammonia/ethanol solution containing the oligoribonucleotide which has passed into the liquid phase is then separated from the glass support and evaporated. Removal of the silyl groups takes place in the presence of tetrabutylammonium fluoride (TBAF) at room temperature for sixteen hours. The TBAF is then neutralized with TEAA (triethylammonium acetate). Other methods include, for example, to so-called phosphotriester, phosphodiester, H-phosphonate, and phosphite methods.

As is apparent, despite the advantages that have been achieved in DNA and RNA syntheses, the art is in need of a multifunctional solid support that could be used to synthesize any oligonucleotide regardless of the nature of the 3'-terminal base.

SUMMARY OF THE INVENTION

The present invention is based, in part, on the development of universal solid supports suitable for use in synthesizing of oligonucleotides. The solid supports are universal in that they may be used irrespective of the first RNA or DNA nucleotide to be synthesized, and irrespective of the type of monomer reagent used during the synthesis, that is, irrespective of the type of substitution on the phosphate group in the 3' position or in the 5' position depending on whether the synthesis is carried out in the 5'→3' or 3'→5' direction.

The novel solid supports of the present invention can be employed in automated solid phase syntheses suing standard process conditions. In particular, with the present invention, the monomer reagent serving to attach the first nucleotide to the solid support should be a monomer reagent identical to the monomer reagent serving to attach the other nucleotides of the sequence during the synthesis, in particular as regards the 5' protection and the 3' protection.

With the present invention, the first nucleotide that is introduced contains a 3' or 5' phosphate group which is, after cleavage between the support and the oligonucleotide, under the usual conditions of deprotection in basic medium, capable at the end of the synthesis of liberating an end 3' or 5' OH. In one aspect, the invention is directed to multifunctional substrates suitable as a reagent for synthesizing oligonucleotide acids have the following formulae:

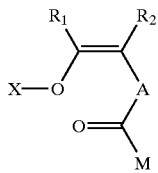

One feature of the invention is that following synthesis of the oligonucleotide, deprotection of the protecting groups and cleavage of the oligonucleotide from the solid support is accomplished with treatment with a standard basic medium such as $NH_4OH$, NaOH.

DETAILED DESCRIPTION OF THE PREFERRED EMBODIMENTS

Substrates suitable as a reagent for synthesizing oligonucleotide acids have the following formulae:

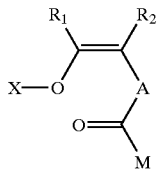

$R_1$, $R_2$: alkyl, cycloalkyl, heteroaryl, aryl, heterocyclic. $R_1$ and $R_2$ may be fused to from an aryl ring (preferably a phenyl ring), heteroaryl ring, heterocyclic ring or cycloalkyl ring, heterocyclic ring or cycloalkyl ring.

X: H or Z (protecting group)
  Z: the protecting group can be acid labile, base labile or photolabile.
    Acid labile: some are cited here for reference but not limited to: trityl, monomethoxytrityl, dimethoxytrityl
    Base labile: some are listed here for reference but not limited to: 9-fluorenylmethyl chloroformate.
    Photolabile: some are listed here for reference but not limited to: m-nitrophenylcarbamate.

A: Heteroatom: O, N, S.

Where M is represented by L-W, where W is preferably a solid substrate (organic and/or inorganic) such as controlled pore glass (CPG), alkylamine CPG, wherein alkyl can be from 1 to 50 carbon atoms, and isomeric forms thereof, any chemical modifications of CPG, wherein the modification can be, for example, amines, hydroxyls, carboxyls, sulfuhydryls, or disulfides, copolymers of styrene and divinylbenzene and any solid support stable to all the conditions of solid phase oligonucleotide synthesis, W can also be a non-solid phosphoramidite group, $—OP(OR_c)NR_4R_5$, where $R_c$ is $—CH_3$, $—CH_2CH_2CN$, or alkane of 1 to 50 carbon atoms, inclusive, and isomeric forms thereof, and $R_4$, $R_5$ is methyl, ethyl, isopropyl, or alkane as defined above (if W is a non-solid phosphoramidite group, it is not restricted to the 3' terminus) and L is a cleavable linking arm connecting carbon C to W which can be any combination of atom groups, (e.g., $—CO(CH_2)_n—$, $—CO_2—$, $—CONH—$, $—COS—$) that covalently connects to the solid phase (W) through a cleavable linkage, and is stable to all the conditions of solid phase oligonucleotide synthesis. Cleavable linkages include esters, amides, thioester, carbamate, carbonate, which are cleaved with ammonium hydroxide. After oligonucleotide synthesis, cleavage of L from the solid phase results in the transfer of the entire multifunctional linking arm to the 3' terminus of the synthesized oligonucleotide. $R_1$, $R_2$ are independently selected from H or an inert group. The term "inert group" refers here to a group that does not react under the conditions encountered during the various steps of the synthesis according to the invention of nucleic acids on a solid support. The inert group preferably is, for example, an alkyl group which is optionally substituted, in particular with one or more halogen(s).

"Cycloalkyl" refers to cyclic alkyl groups of from 3 to 10 carbon atoms having a single cyclic ring or multiple condensed rings that can be optionally substituted with from 1 to 3 alkyl groups. Such cycloalkyl groups include, by way of example, methylcyclopropyl, 2-methylcyclopentyl, 2-methylcyclooctyl, and the like, or multiple ring structures such as adamantanyl, and the like.

"Heteroaryl" refers to a monovalent aromatic carbocyclic group of from 2 to 8 carbon atoms and 1 to 4 heteroatoms selected from oxygen, nitrogen and sulfur within the ring. Unless otherwise constrained by the definition for the heteroaryl substituent, such heteroaryl groups can be optionally substituted with 1 to 3 substituents selected from the group consisting of alkyl, alkoxy, aryl, aryloxy, halo, nitro, heteroaryl, thioalkoxy, thioaryloxy and the like. Such heteroaryl groups can have a single ring (e.g., pyridyl or furyl) or multiple condensed rings (e.g., indolizinyl or benzothionyl). Preferred heteroaryls include pyridyl, payroll and furyl. "Heterocyclo" or "heterocyclic" refers to a monovalent saturated or unsaturated group having a single ring or multiple condensed rings, from 1 to 8 carbon atoms and from 1 to 4 heteroatoms selected from nitrogen, sulfur or oxygen within the ring. Unless otherwise constrained by the definition for the heterocyclic substituent, such heterocyclic groups can be optionally substituted with 1 to 3 substituents selected from the group consisting of alkyl, alkoxy, aryl, aryloxy, halo, nitro, heteroaryl, thioalkoxy, thioaryloxy and the like. Such heterocyclic groups can have a single ring or multiple condensed rings. Preferred heteroaryls include morpholine, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanathroline, isothiazole, phenazine, isoxazole, phenoxazine, phenothiazine, imidazolidine, imidazoline, piperidine, piperazine, indoline, morpholine, piperidinyl, tetrahydrofuranyl, and the like.

In a preferred embodiment, the substrates have the following formulae:

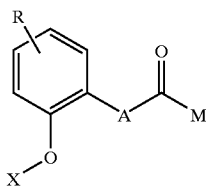

R: —H, any withdrawal electron group as: —CN, —NO$_2$, —CO—R$_1$, —CONH—R$_1$, F, Cl, Br, I
Alkyl or aryl group.
Any electron donor group as: —OH, —OR, —NH$_2$, —NHR
—R$_1$: H, alkyl, aryl
M: same definition as above
X: same definition as above In a particularly preferred embodiment, the substrate has the structure:

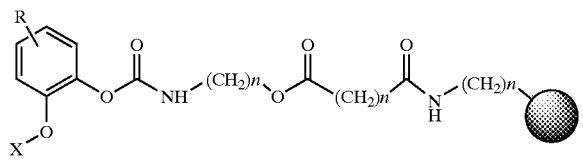

R: H, —OCH$_3$, —CONH—R$_1$, —CO$_2$R$_1$, —COR$_1$
n: 1 to 12
X: Trityl, monomethoxytrityl, dimethoxytrityl
⬤: Solid Support The inventive substrates can be employed to synthesize nucleic acids, in particular the automatic synthesis, using conventional techniques. The inventive solid support, can especially be exploited for the manufacture of oligonucleotides modified at the terminal 3' end by using directly, in the first cycle, monomers corresponding to the desired nature of the modification.

The term "nucleic acid" refers to deoxyribonucleic acids or ribonucleic acids or, more generally, polynucleotides or oligonucleotides in which the bases, internucleotide phosphate bonds or the ribose rings of the bases may be chemically modified in a known manner. They may in particular be oligonucleotides of alpha or beta anomers, oligonucleotides of internucleotidic bonding of the phosphorothioate or methyl phosphonate type, or alternatively oligothionucleotides.

In one particular embodiment, the process of the invention comprises the following steps of:
1) condensation of the 5' or 3' OH group of the first nucleotide or of an oligonucleotide connected at its other 3' or 5' end to the said solid support, using a coupling agent, with the phosphonate group optionally substituted in the 3' or 5' position, respectively, of a nucleotide monomer reagent protected in the 3' and 5' positions;
2) oxidation or sulfurization of the internucleotide bond of the phosphite type obtained in step 1) to a phosphate bond, respectively;
3) deprotection of the 5'-O or 3'-O end of the product obtained in step 2);
4) repetition of steps 1) to 3) as many times as there are nucleotides to be added in order to synthesize the nucleic acid.

More precisely, the process may comprise the following steps of:

1) condensation using a coupling agent, of the said SH group of the said solid support with a phosphate or phosphite group optionally substituted in the 3' or 5' position of a nucleotide monomer reagent protected in the 5'O and 3'-O position;
2) oxidation or sulfurization of the covalent bond of the phosphite type between the solid support and the first nucleotide obtained in step 1);
3) deprotection of the 5'-O or 3'-O end of the product obtained in step 2);
4) condensation of the 5'OH or 3'OH group of the product obtained in step 3) with the phosphate, phosphorothioate or phosphite group optionally substituted in the 3' or 5' position of a nucleotide monomer reagent protected in the 5'-O or 3'-O position, respectively, using the said coupling agent, under the same conditions as in step 1);
5) oxidation or sulfurization of the internucleotide grouping of the phosphite type resulting from the above step into a grouping of the phosphate or phosphorothioate type, respectively;
6) deprotection of the 5'-O or 3'-O end of the product obtained in step 5);
7) repetition of steps (4), (5) and (6) as many times as there are nucleotides to be added in order to obtain the nucleic acid to be prepared.

The above steps lead to an nucleotide connected to the solid support. In an appropriate manner, the process according to the invention includes a final step of detachment of the nucleic acid from the support and removal of the protecting groups from the bases and, where appropriate, from the 2'-O positions of the nucleic acid.

In the prior techniques in which the solid support is already connected to a first nucleoside corresponding to the first nucleotide of the sequence to be prepared, before starting the synthetic cycles, the said support generally contains protection of the said nucleoside in the 5' or 3' position. In this case, the synthetic cycle begins with a step of deprotection in acid medium, generally a detritylation with TCA, DCA or TCA in dichloromethane.

SYNTHESIS OF INVENTIVE SUBSTRATES

It should be noted that only the main reaction products are shown. The reactions were conducted at ambient temperature (about 22° C.) and were monitored by TLC.
Synthesis of:

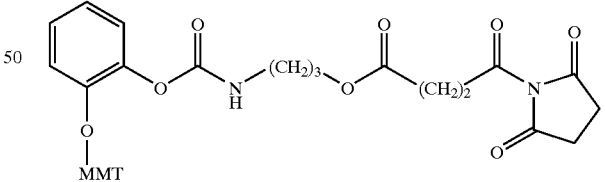

a/ 110 mg (1 mmol) of catechol was dissolved in 3 ml of tetrehydrofuran (THF) and 140 umol (1 mmol) of triethylamine (TEA). 309 ml (1 mmol) of monomethoxytrityl chloride was added slowly to the solution and allowed to react for about 30 min. at room temperature. The salt (TEA.HCl) formation was filtered and the crude solution is used as it is for the next step.
b/ Added 85 ul (1 mmol) of pyridine (1 mmol) to the filterate solution and 202 mg (1 mmol) of paranitrophenylchloroformate (PNCF) was added to the solution and it was kept under stirring for 30 min. at room temperature. Filtered the salt (pyridine HCl) formed and used the filterate solution for the next step.

c/ Added 76.5 ul of 3-aminopropanol followed by addition of 140 ul of TEA (1 mmol). The reaction solution was agitate for 12 hours at room temperature. After the agitation, evaporated the solvent then purified the crude by flash chromatography to obtain the desired intermediate (I1):

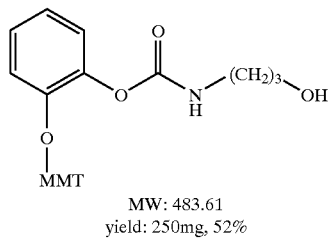

MW: 483.61
yield: 250mg, 52% d/ Dissolved 242 mg of (I1) (0.5 mmol) in 5 ml of acetonitrite. 50 mg of succimic anhydride (0.5 mmol) and 40 ul of pyridine was added to the solution and allowed to react overnight. The product was coevaporated with acetonitrite (2×). The following intermediate (I2) was obtained with 100% yield.

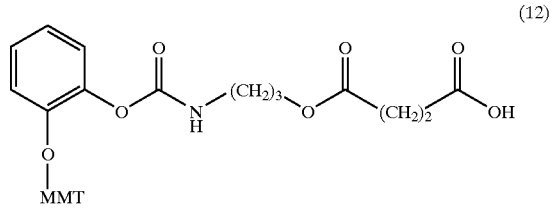

e/ Dissolved the obtained (I2) in 5 ml of Acetonitrite and 57.5 mg (0.5 mmol) of N-hydroxysuccinimide was added to the solution and allowed to react for about 2 hours. The urea was filtered and the solution was evaporated to give a pure final product with 100% yield:

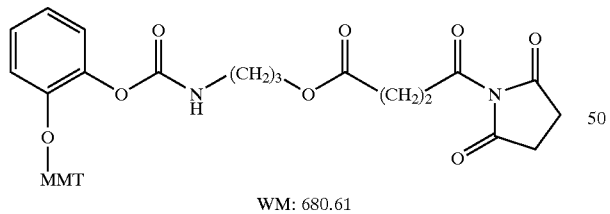

WM: 680.61

The desired product was used to derivatize the CPG with aminolinker arm on c) as follow:

−1 g of CPG-NH$_2$ is added to the solution made of 5 ml of acetonitrite, 140 mg product (200 umol), 100 ul of triethylamine and the reaction was allowed to proceed for 3 hours at ambient temperature

SYNTHESIS OF OLIGONUCLEOTIDE

The following scheme illustrates oligodeoxyribonucleotide synthesis by the phosphoramidite method with the inventive substrate using standard conditions. Phosphoramidite chemistry is well known and is described in U.S. Pat. Nos. 4,725,677; 4,458,066; 4,415,732, WO 95/10987, and BioTechniques Vol. 22, No. 4 pp 752–756, 1997, which are incorporated herein

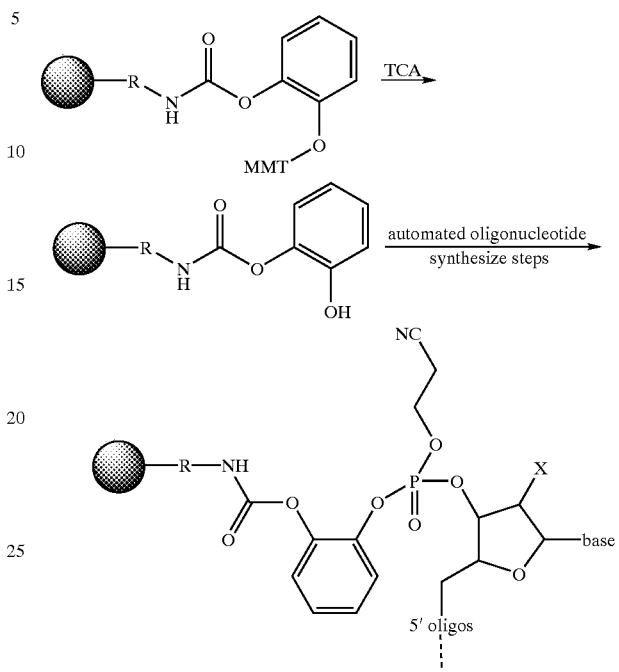

The synthesized oligonucleotides is then cleaved and deprotected with basic media as (NH$_4$OH), leaving a 3'OH end suitable for any use as shown below.

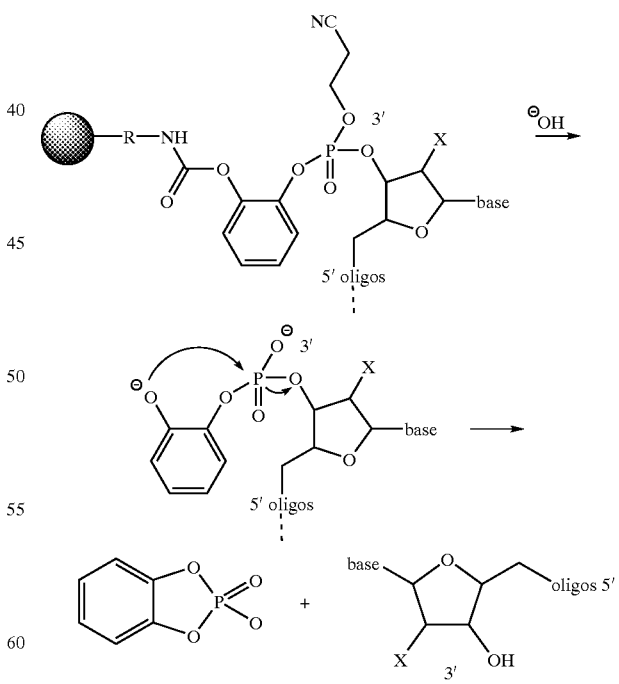

Solid support (silica gel or polymeric substrate)
R: linker which is a hydrocarbon chain, containing CHNO
DMT: dimethoxytrityl Base: A=Adenine
G=Guanine
C=cytosine
T=Thymine
U=uracil X: H or $OR_1$ with $R_1$ is hydrocarbon structure (C, H, N, O) and/or

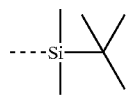

Although only preferred embodiments of the invention are specifically disclosed and described about, it will be appreciated that many modifications and variations of the present invention are possible in light of the about teachings and within the preview of the appended claims without departing from the spirit and intended scope of the invention.

What is claimed is:

1. A process for oligonucleotide syntheses wherein nucleotides are incorporated onto a substrate that is represented by the following formulae:

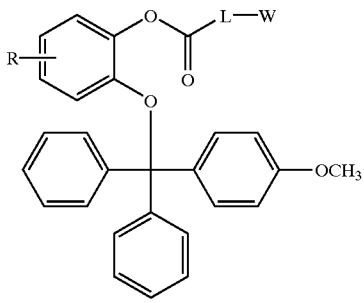

where W is selected from the group consisting of organic solid substrates and inorganic solid substrates and L is a cleavable linking arm covalently connecting W to a carbon that is stable in oligonucleotide synthesis conditions and R is an alkyl or alkoxy.

2. The process of claim 1 wherein said substrate is represented by the formulae:

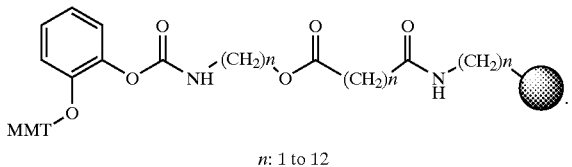

n: 1 to 12

3. The process of claim 2 comprising the steps of (i) attaching a first nucleotide to the solid substrate and (ii) attaching a second nucleotide to the first nucleotide via a condensation reaction while the first nucleotide is bonded to the substrate wherein both steps use a monomer reagent that is the same.

4. The process of claim 2 comprises the steps of:
a) condensation of the 5' or 3' OH group of a first nucleotide or of an oligonucleotide connected at its other 3' or 5' end to the said solid support, using a coupling agent, with the phosphate group optionally substituted in the 3' or 5' position respectively of a monomer nucleotide reagent protected in the 3' and 5' positions;
b) oxidation or sulfurization of the internucleotide bond of the phosphite type obtained in step a) to a phosphate or phosphorothioate bond, respectively;
c) deprotection of the 5'-O or 3'-O end of the product obtained in step b);
d) repeating steps a) to c) as desired to synthesize the nucleic acid.

5. The process of claim 2 comprising the steps of:
a) condensation, using a first coupling agent, of an OH group of the solid support with a phosphate or phosphite group optionally substituted in the 3' or 5' position of a monomer nucleotide reagent protected in the 5'-O and 3'-O positions;
b) oxidation or sulfurization of the covalent bond of the phosphite type between the solid support and first nucleotide obtained in step a);
c) deprotection of the 5'-O or 3'-end of the product obtained in step b);
d) condensation of the 5'OH or 3'OH group of the product obtained in step c) with the phosphate, phosphorothioate or phosphite group optionally substituted in the 3' or 5' position of a monomer nucleotide reagent protected in the 5'-O or 3'-O position, respectively, using the said first coupling agent;
e) oxidation or sulfurization of the internucleotide grouping of the phosphite type resulting from the above step d into a grouping of the phosphate or phosphorothioate type, respectively;
f) deprotection of the 5'-O or 3'-O end of the product obtained in step e);
g) repeating steps d), e), and f) as desired to synthesize the nucleic acid.

6. The process of claim 5 including a step of detaching of the nucleic acid from the substrate and removing of the protecting groups from the bases and, where appropriate, from the 2'-O positions of the nucleic acids.

7. The process of claim 6 wherein detaching the nucleic acid and removing the protecting groups comprise treating the product of step g) with base.

8. The process of claim 7 wherein the base is selected from the group consisting of $NH_4OH$, NaOH, and methylamine.

9. The process of claim 1 wherein the solid substrate is selected from the group consisting of controlled pore glass (CPG), and alkylamine CPG.

10. A process for oligonucleotide syntheses wherein nucleotides are incorporated onto a substrate that is represented by the following formulae:

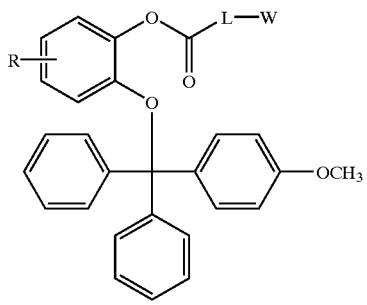

where W is a liquid phase phosphoramidite group represented by $-OP(OR_3)NR_4R_5$ wherein $R_3$ is $-CH_3CH_2CH_2CN$, or an alkyl having 1 to 50 carbon atoms, and $R_4$ and $R_5$ each independently selected from isopropyl or alkyl having 1 to 50 carbon atoms and L is a cleavable linking arm covalently connecting a W to a carbon and is stable is oligonucleotide synthesis conditions, and wherein R is hydrogen —CN, $NO_2$, —CO—$R_1$—CONH$R_1$, F, Cl, Br, I, alkyl, aryl, —OH, —OR, —$NH_2$, —NHR wherein —R is hydrogen, alkyl or aryl.

11. The process of claim 10 wherein said substrate is represented by the formulae:

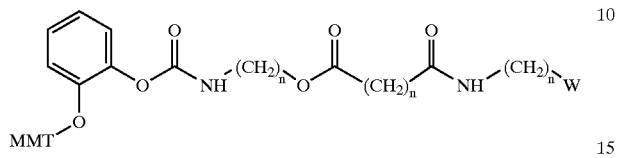

wherein n is an integer of 1 to 12.

12. The process of claim 11 comprising the steps of (i) attaching a first nucleotide to the substrate and (ii) attaching a second nucleotide to the first nucleotide via a condensation reaction while the first nucleotide is bonded to the substrate wherein both steps use a monomer reagent that is the same.

13. The process of claim 11 comprises the steps of:
a) condensation of the 5' or 3' OH group of a first nucleotide or of an oligonucleotide connected at its other 3' or 5' end to the said substrate, using a coupling agent, with the phosphate group optionally substituted in the 3' or 5' position respectively of a monomer nucleotide reagent protected in the 3' and 5' positions;
b) oxidation or sulfurization of the internucleotide bond of the phosphite type obtained in step a) to a phosphate or phosphorothioate bond, respectively;
c) deprotection of the 5'-O or 3'-O end of the product obtained in step b);
d) repeating steps a) to c) as desired to synthesize the nucleic acid.

14. Process of claim 11 comprising the steps of:
a) condensation, using a first coupling agent, of an OH group of the substrate with a phosphate or phosphite group optionally substituted in the 3' or 5' position of a monomer nucleotide reagent protected in the 5'-O and 3'-O positions;
b) oxidation or sulfurization of the covalent bond of the phosphite type between the solid support and first nucleotide obtained in step a);
c) deprotection of the 5'-O or 3'-end of the product obtained in step b);
d) condensation of the 5'OH or 3'OH group of the product obtained in step c) with the phosphate, phosphorothioate or phosphite group optionally substituted in the 3' or 5' position of a monomer nucleotide reagent protected in the 5'-O or 3'-O position, respectively, using the said first coupling agent;
e) oxidation or sulfurization of the internucleotide grouping of the phosphite type resulting from the above step d into a grouping of the phosphate or phosphorothioate type, respectively;
f) deprotection of the 5'-O or 3'-O end of the product obtained in step e);
g) repeating steps d), e), and f) as desired to synthesize the nucleic acid.

15. The process of claim 14 including a step of detaching of the nucleic acid from the substrate and removing of the protecting groups from the bases and, where appropriate, from the 2'-O positions of the nucleic acids.

16. The process of claim 15 wherein detaching the nucleic acid and removing the protecting groups comprise treating the product of step g) with base.

17. The process of claim 16 wherein the base is selected from the group consisting of $NH_4OH$, NaOH, and methylamine.

* * * * *